United States Patent [19]
Smith et al.

[11] Patent Number: 6,141,625
[45] Date of Patent: Oct. 31, 2000

[54] VISCOMETER MODULE WITH CRYSTAL RESONATOR-TYPE SENSOR

[75] Inventors: Ronald L. Smith, Troy; Mark Lovik, Chatham, both of Ill.

[73] Assignee: DICKEY-john Corporation, Auburn, Ill.

[21] Appl. No.: 09/090,363

[22] Filed: Jun. 4, 1998

Related U.S. Application Data

[63] Continuation-in-part of application No. 08/871,272, Jun. 9, 1997, abandoned.

[51] Int. Cl.$^7$ ........................................................ G01N 9/00
[52] U.S. Cl. ............................................. 702/50; 73/54.01
[58] Field of Search ............................... 702/50, 54, 56, 702/103; 73/1.02, 32 A, 40.5 A, 75.5, 54.01, 54.02, 54.41, 64.53

[56] References Cited

U.S. PATENT DOCUMENTS

| | | | |
|---|---|---|---|
| 4,065,959 | 1/1978 | Richardson | 73/56 |
| 4,484,468 | 11/1984 | Gau et al. | 73/60 |
| 4,741,200 | 5/1988 | Hammerle | 73/54 |
| 4,783,987 | 11/1988 | Hager et al. | 73/32 A |
| 5,198,716 | 3/1993 | Godshall et al. | 310/349 |
| 5,201,215 | 4/1993 | Granstaff et al. | 73/54.41 |
| 5,365,778 | 11/1994 | Sheen et al. | 73/54.41 |
| 5,416,448 | 5/1995 | Wessendorf | 331/116 R |
| 5,503,003 | 4/1996 | Brookfield | 73/54.32 |
| 5,526,287 | 6/1996 | French | 364/550 |
| 5,541,855 | 7/1996 | Enzler et al. | 364/552 |
| 5,734,098 | 3/1998 | Kraus et al. | 73/61.62 |
| 5,741,961 | 4/1998 | Martin et al. | 73/32 R |
| 5,798,452 | 8/1998 | Martin et al. | 73/32 R |
| 5,827,952 | 10/1998 | Mansure et al. | 73/61.45 |
| 5,839,094 | 11/1998 | French | 702/91 |

FOREIGN PATENT DOCUMENTS

WO 97/49980   12/1997   WIPO .

OTHER PUBLICATIONS

"Viscosity—Part 1," *Measurements & Control*, Sep. 1994, pp. 114–119.
"Viscosity—Part 2," *Measurements & Control*, Oct. 1994, pp. 70–75
"Viscosity—Part 3," *Measurements & Control*, Dec. 1994, pp. 69–73.
S.J. Martin et al., "Characterization Of A Quartz Crystal Microbalance With Simultaneous Mass And Liquid Loading," *Analytical Chemistry*, vol. 63, No. 20, Oct. 15, 1991, pp. 2272–2281.
S. Bruckenstein et al., "Dual Quartz Crystal Microbalance Oscillator Circuit. Minimizing Effects Due To Liquid Viscosity, Density, And Temperature," *Analytical Chemistry*, vol. 66, No. 11, Jun. 1, 1994, pp. 1847–1852.
"Monitoring Corrosivity In The Atmosphere With A QCM," *J. Electrochem. Soc.*, 1996, 143.
W. Lee et al., "Depletion Layer Effects On The Response Of The Electrochemical Quartz Crystal Microbalance," *Analytical Chemistry*, vol. 65, No. 22, Nov. 15, 1993, pp. 3232–3237.
J. Redepenning et al., "Osteoblast Attachment Monitored With A Quartz Crystal Microbalance," *Analytical Chemistry*, vol. 65, No. 23, Dec. 1, 1993, pp. 3378–3381.
A.C. Hillier et al., "Scanning Electrochemical Mass Sensitivity Mapping Of The Quartz Crystal Microbalance In Liquid Media,"*Analytical Chemistry*, vol. 64, No. 21, Nov. 1, 1992, pp. 2539–2554.

(List continued on next page.)

*Primary Examiner*—Patrick Assouad
*Attorney, Agent, or Firm*—Katten Muchin Zavis

[57] ABSTRACT

A portable viscometer includes an instrument body having an electrical control circuit disposed therein and sensor probe for immersion into a fluid to be analyzed. The sensing probe includes a crystal resonator-type sensor and a temperature sensor that provide sensing signals to the electrical control circuit indicative of fluid viscosity. The resultant viscosity is displayed and/or stored.

8 Claims, 10 Drawing Sheets

OTHER PUBLICATIONS

T. Scarlett, "Viscosity, Yield Value Prime Ink Qualities," *American Printer,* Dec. 1994, vol. 214, n3, p. 72(1).

S. Berne, "In–Line System Automatically Determines Product Viscosity,"*Prepared Foods,* Oct. 1994, vol. 163, n. 11, p. 115.

G. Tucker, "Visosity: How Can It Be Measured?", *Food Manufacture,* Jun. 1993, vol. 68, n6, p. 49.

D. Holland, "Rheological Measurements Of Pharmaceutical Products Moisturizing Milks," *Cosmetics and Toiletries,* Mar. 1992, vol. 107, n3, p. 49.

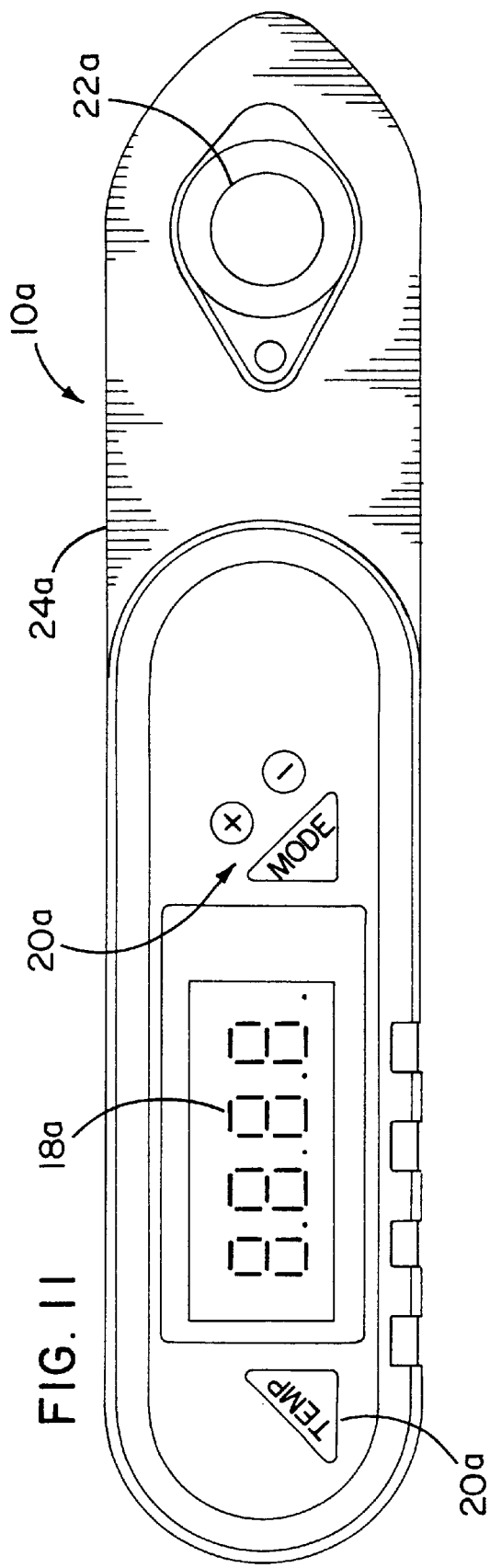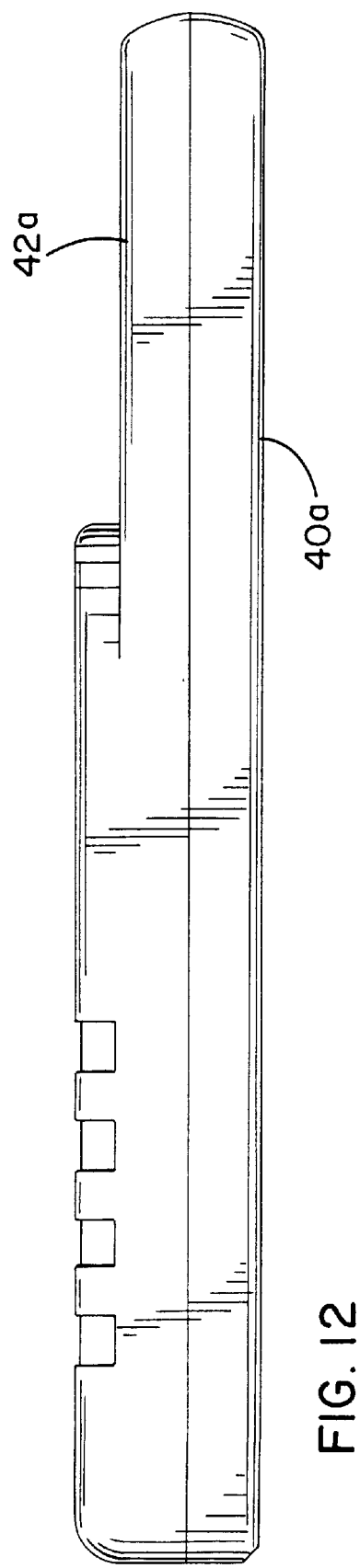
FIG. 11
FIG. 12

VISCOMETER MODULE WITH CRYSTAL RESONATOR-TYPE SENSOR

CROSS REFERENCE TO RELATED APPLICATIONS

This application is a continuation-in-part of U.S. application Ser. No. 08/871,272, filed Jun. 9, 1997, abandoned.

FIELD OF THE INVENTION

The present invention relates generally to the sensor art, and in particular, to a hand-held viscosity measurement device with a crystal resonator-type sensor and control circuitry, all of which may be contained in a single enclosure.

BACKGROUND OF THE INVENTION

Most fluids have a resistance to flow which is characterized as viscosity. The higher the resistance to flow, the higher the viscosity. For example, flow is measured in most materials by applying a shear force or stress and measuring the resulting shear rate. Viscosity can thus be characterized as the ratio of the shear stress and the shear rate. The ratio of applied shear rate resulting from the applied shear stress is known as the absolute viscosity, or dynamic viscosity. Viscometers that measure absolute viscosity apply a shear force and measure the resulting drag or damping. Other viscometers measure viscosity by timing the flow of a given volume of fluid without imposing external forces. The flow is the result of the hydrostatic head of the material. This type of viscosity measurement is kinematic viscosity. The relationship between absolute viscosity ($\eta$) and kinematic viscosity ($\nu$) is given by:

$$\nu = \eta/\rho$$

where $\rho$ is the density of the fluid.

However, viscosity has been generally difficult to measure for several reasons relating to the physical nature of the fluid under investigation such as the shear rate or viscosity gradient, temperature, and density. Shear rate due to applied forces such as the forces applied by mixers, pumps, gravity, and the like effects fluid viscosity differently for different fluids. The viscosity of fluids such as water or oil remains constant regardless of changes in shear rate and are more predictable in handling. Other fluid viscosities change with a change in shear rate. The fluid characteristics are not proportional to the change in shear rate (i.e., paint becomes thinner when stirred).

In addition, temperature greatly effects viscosity by altering the kinetic energy of a fluid. Typically, as fluids become warmer, viscosity decreases. For this reason, a viscosity index of the fluid is used to characterize the rate of change in viscosity. Viscosity can change by more than +/−5% with a 1 degree C. change in temperature. Likewise, density effects the viscosity when the effects of gravity are taken into account (i.e., the weight of the fluid above an orifice effects the speed with which the fluid flows through the orifice).

Various viscosity measurement technologies are known in the art. One type of known mechanical viscometer utilizes efflux cups to measure kinematic viscosity. An operator fills the cup of the instrument, then times the period for the cup to empty. Bubble time, falling needle, falling ball, and falling element-type instruments are other examples of low-cost time-based measurement. In these instruments, the operator fills a chamber with the fluid sample, then times the period for a bubble to rise or a needle to fall. While these instruments are useful for simple qualitative testing, the timing of the test is susceptible to a degree of variability. Non-Newtonian and particulate-laden fluids are also difficult to measure with these instruments. Moreover, a rather large quantity of fluid is required to satisfactorily perform the test.

Higher accuracy devices are available primarily in laboratory setups such as those which use glass capillary action. While they are generally more elaborate than the lower cost mechanical systems, they nevertheless operate on a time-based measurement. In addition, complex setup of the instrumentation is usually required.

Other viscometers utilize electromechanical sensors to measure absolute viscosity. These instruments sometimes use rotating cups, piston or vibratory arms, or rotating spindles to apply a known shear force to the fluid and monitor the response of the system. Such instruments still have difficulty resolving lower viscosity ranges, and require insertion into the liquid being measured or require relatively large fluid samples. For example, one type of electromechanical sensor employs coils that generate a magnetic force to move a piston back and forth. This instrument analyzes the travel time of the piston to measure absolute viscosity. However, clean up can be difficult depending on the design of the instrument.

Still other oscillating types of viscosity measurement devices use spheres or probes that oscillate at a desired rate. Circuitry is disposed to measure the dampening of oscillation to measure absolute viscosity. Although a wide range of viscosity measurement is possible, portability of these devices is often difficult. Likewise, these instruments often require a large sample volume to perform the measurement.

While these systems perform satisfactorily in laboratory or for the particular capacities for which they are intended, they suffer from requiring relatively large fluid samples and are primarily embodied in in-situ laboratory setups and the like. Thus, it is desirable to have a portable viscometer that is capable of quick response with small fluid sample requirements, while being highly accurate.

SUMMARY OF THE INVENTION

Accordingly, it is a general object of the invention to provide a viscosity measuring instrument that overcomes the deficiencies of the prior art.

It is a further object of the invention to provide a viscometer that requires a reduced fluid samples.

It is yet another object of the invention to provide a viscometer that utilizes a crystal resonator-type sensor construction.

It is another object of the invention to provide a viscometer that is portable and which is relatively lightweight in construction.

The present invention provides these and other additional objects and advantages in a portable viscometer. The viscometer comprises a relatively compact instrument body with a portion that is adapted for ready hand access. The body contains an electrical control circuit having a display and input that are also accessible by the user. A sensing circuit including a crystal resonator sensing element is located in a sensor housing remote from the instrument body in one embodiment. In another embodiment, the electrical control circuit and sensing circuit are contained within a single enclosure. This arrangement is adapted to detect the viscosity of a fluid in which it is immersed. Preferably, the temperature of the fluid is also detected. Sensing signals indicative of at least the viscosity are provided to the electrical control circuit. In the preferred embodiment, the electrical control circuit converts the sensing signals to digital data which is output to the display in one mode of operation. In this way, fluid viscosity may be readily detected.

BRIEF DESCRIPTION OF THE DRAWINGS

FIG. 11 is a top view of a portable viscometer construction according to another preferred embodiment of the present invention;

FIG. 12 is a side view of the embodiment of FIG. 11; and

DETAILED DESCRIPTION OF THE INVENTION

Generally, the present invention relates to a hand-held viscometer that includes a crystal resonator-type sensor. The invention is a relatively lightweight and compact design that may be embodied in a portable unit to enable use in a wide variety of applications where the viscosity of a fluid is to be measured. For example, it is contemplated that the invention may be used for very precise measurement of viscosity in laboratory settings and the like. Similarly, the invention may be used in manufacturing facilities or by agricultural or maintenance personnel. According to one feature of the invention, the viscometer includes a display menu that may be readily utilized by the user to access various measurement or display options as desired.

Figure 1:
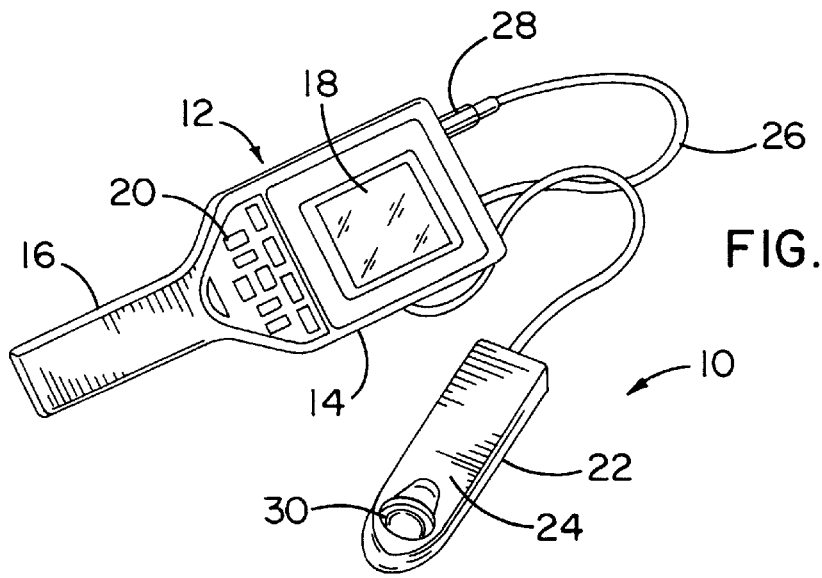
FIG. 1 is a perspective view of a portable viscometer construction according to one embodiment the present invention.
Figure 2:
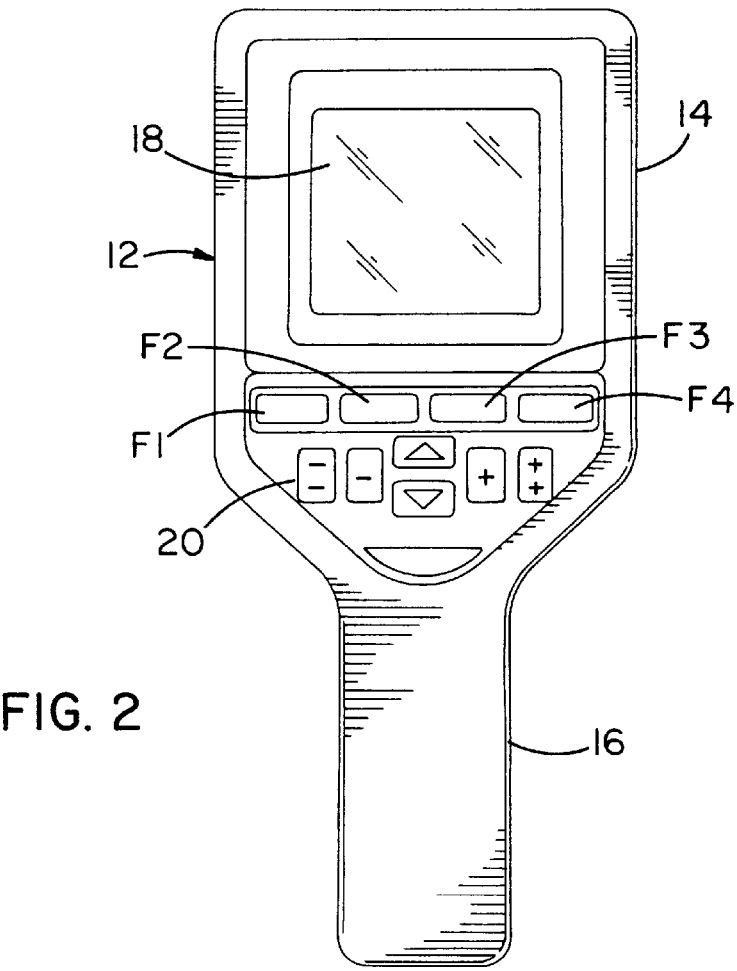
FIG. 2 is a front view of an instrument housing of the viscometer shown in FIG. 1.

FIG. 1 illustrates a portable viscometer 10 according to one embodiment of the invention. The viscometer 10 comprises a lightweight instrument housing 12 including a generally rectangular enclosure or body 14 with a handle 16 depending from one side of the body. The handle 16 ready hand access to the housing 12. As described below, the housing contains an electrical control circuit which provides output signals to an instrument display 18, located on a facing surface of the instrument body 14. A user input interface 20 that enables various user selection and options is also located on a facing surface of the body 14 proximate to the handle 16. FIG. 2 shows a front view of the instrument housing 12. As seen therein, the input interface 20 comprises a keypad with various function keys F1–F4. In addition, various scrolling keys are included on the interface, as described in greater detail below.

A sensor probe construction 22 designed to be contacted by fluid under investigation is disposed at a location remote from the body 12. The sensor probe 22 similarly includes a sensor housing or enclosure 24 that contains a crystal resonator-type sensor, a temperature sensor, and sensing circuitry as described below. As shown in FIG. 1, a portion of the sensor 30 is exposed from the interior of the sensor housing so that it may be placed in contacting relation with the fluid sample under investigation.

In accordance with one feature of the invention, a connection cable 26 detachably couples the sensor probe 22 with the electrical control circuit disposed in the instrument body 14. The cable terminates with a suitable electrical connector plug 28 that mates with a complemental jack disposed in the instrument housing 12. This permits the sensor probe 22 to be easily removed during transport or storage of the instrument. In addition, when fluids of greatly different viscosities are to be measured, the sensor probe may be easily replaced by another probe having a different sensitivity.

Figure 3:
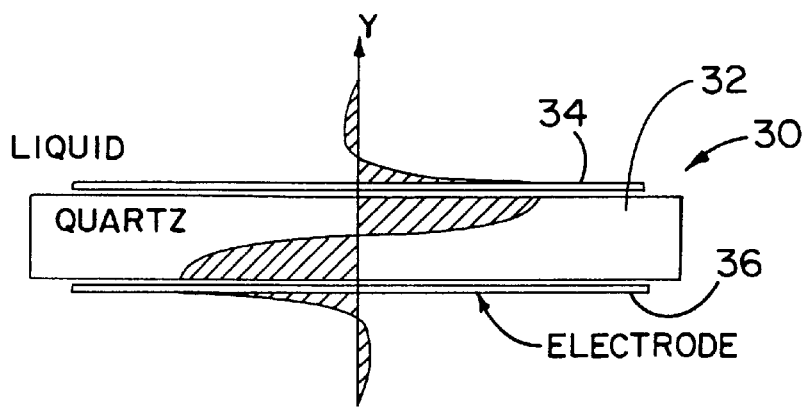
FIG. 3 illustrates a diagrammetric cross section of a crystal resonator-type sensing element used in conjunction with the present invention.
Figure 4:
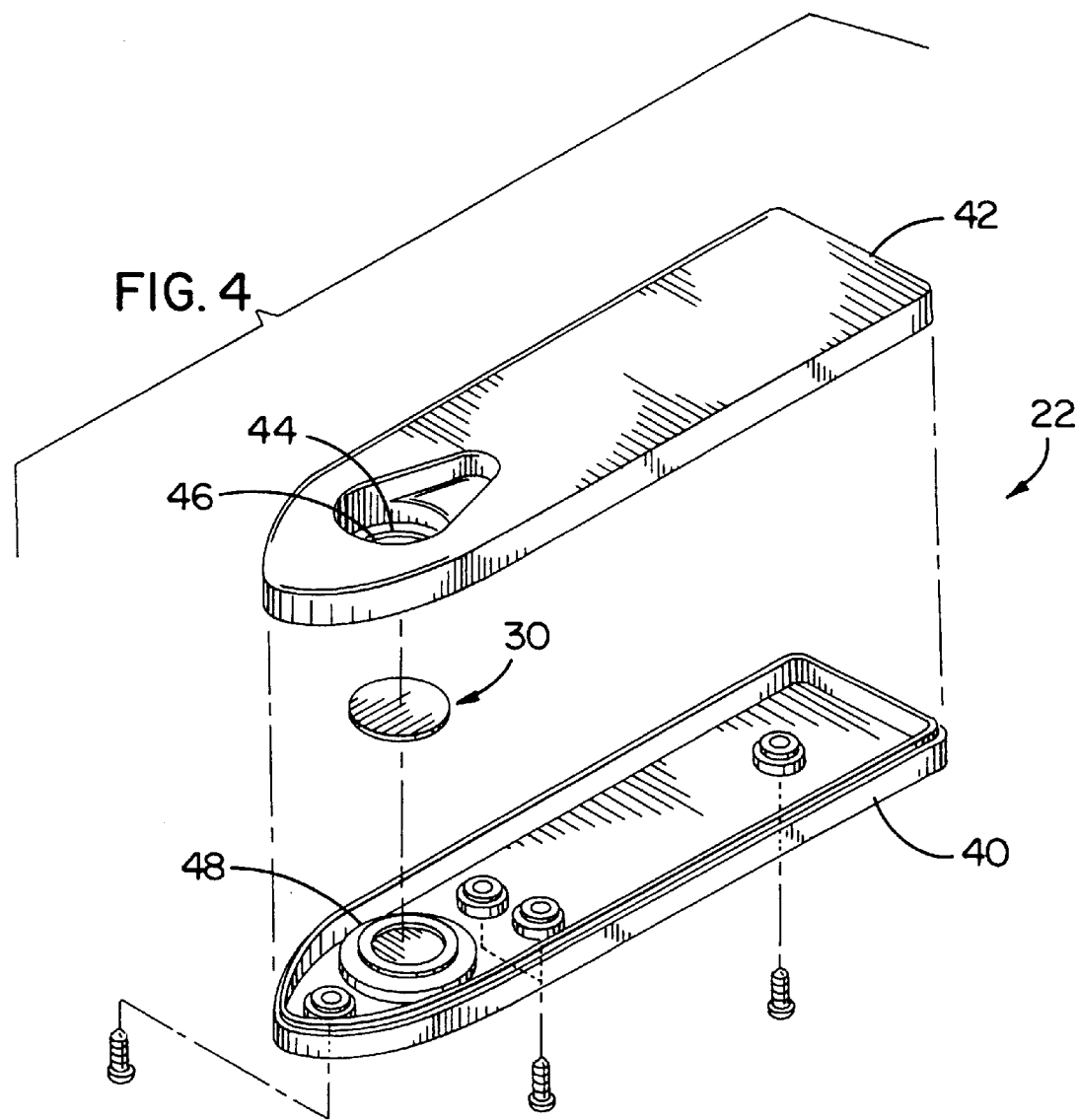
FIG. 4 shows an exploded view of a sensor probe housing suitable for the sensor of FIG. 3.
Figure 5:
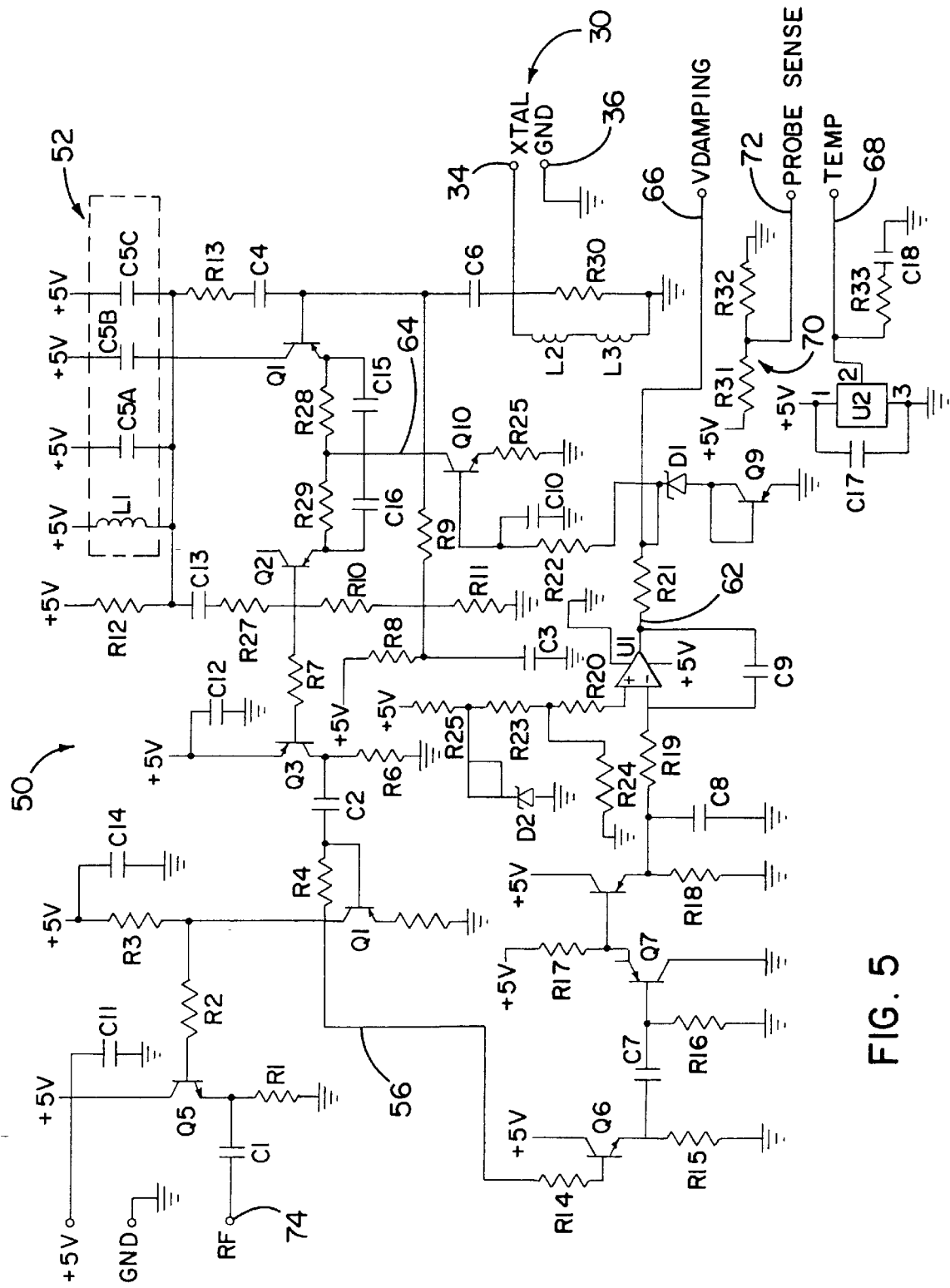
FIG. 5 is an electrical circuit diagram of a sensing circuit used in conjunction with the sensor of FIG. 3 to develop various sensing signals according to the present invention.

The details of the sensor probe 22 and the various components thereof are shown in FIGS. 3 through 5. As seen in FIG. 3, the sensor according to the invention is a crystal resonator-type sensing element 30 having a disk-like diaphragm 32 fabricated from AT cut crystalline quartz. This type of sensor construction is described in detail in U.S. Pat. No. 5,198,716, entitled "Micro-machined Resonator," the subject matter of which is incorporated herein in its entirety. The diaphragm 32 is sandwiched between a pair of electrodes 34, 36 vacuum deposited on the opposed facing surfaces of the diaphragm 32. The electrodes are similarly disk-shaped and are fabricated of gold. The diaphragm is constructed such that there is a known resonance frequency for the crystal that is a function of the quartz geometry.

When appropriate signals are applied to the opposed electrodes 34, 36 to achieve resonance for the crystal, the sensor operates as a thickness shear mode resonator (TSM). This construction is used to measure viscous damping when immersed in a fluid under investigation. That is, the opposite faces of the crystal oscillate in opposed directions where the displacement is parallel to the surface of the crystal as shown in FIG. 3. There is preferably no significant compressional deformation of the sensing element. Any liquid in contact with the crystal will be viscously entrained. Power dissipation in the liquid will cause damping of the crystal resonance. In other words, as the viscosity-density product (of the liquid in contact with the crystal) increases, the resistance of the sensing element increases. The change in resistance is the motional resistance of the sensor, and is directly related to the square root of the viscosity density product of the liquid. Thus, measurement of the resonance damping characteristics has been found to sense viscosity-density of the liquid.

Any solid in contact with the crystal will also lower the resonant frequency of oscillation of the sensor. This frequency shift can also be utilized to determine mass accumulation or contamination on the surface of the sensing element.

FIG. 4 illustrates the sensor probe housing 24 in greater detail. As shown therein, the housing comprises a pair of opposed, complemental housing pieces 40, 42 that are mated together. One of the pieces 42 has a recess 44 formed therein to expose one of the disk-like sensor electrodes 34. When the electrode is in contacting relation with the fluid, the sensor may be idealized as in contact with the fluid. In the preferred embodiment, the sensor is sandwiched between a pair of grommet pieces 46, 48. In this way, the sensor operates in a suspension mode when the housing pieces 40, 42 are mated together. In addition, the arrangement provides a hermetic seal. Alternatively, both sides of the sensor may be exposed to the fluid under investigation such as in low viscosity measurements. In either case, the construction enables the viscosity of the fluid under investigation to be analyzed. It should be understood that a sensing circuit is also located within the probe housing 24 although it has not been shown in FIG. 4 for purposes of clarity.

FIG. 5 illustrates a sensing circuit 50 used to develop various sensing signals corresponding to the viscosity of the analyzed fluid. The circuit 50 comprises an RLC circuit 52 including inductors L1–L3, C5A–C and R30 is tuned to the fundamental resonance frequency of the sensing element. As the sensing element is loaded, it requires additional current in order to continue oscillation. A sensed voltage corresponding to this current is detected.

In particular, a differential current oscillator circuit 54 including a pair of transistors Q1 and Q2 arranged in a push-pull arrangement is coupled with the RLC circuit and is disposed to provide a resonant frequency of oscillation to the sensor electrode 34. Inasmuch as transistors Q1 and Q2 are alternately conducting, a signal is applied to the base terminal of transistor Q2 that corresponds to the frequency of oscillation of the circuit. The signal appearing at the base terminal of Q2 is also provided to the base terminal of transistor Q3,which is connected to the base of transistor via a resistor R7. Transistor Q3 is a high impedance transistor which has its collector terminal connected to +5 volts and its collector terminal connected through resistor R6 to ground.

The signal developed at the emitter terminal of transistor Q3 is supplied via a blocking capacitor C2 to an amplifier circuit including a transistor Q4.In particular, the signal is applied to the base terminal of transistor Q4,which has its collector terminal connected through a feedback resistor R4. The emitter terminal of transistor Q4 is connected through resistor R5 to ground. The signal appearing at the collector terminal of transistor Q4 is an amplified signal that is supplied via a line 56 to a resistor R14 and thereafter to a rectifier circuit 58 including transistors Q6, Q7and Q8. The rectifier circuit 58 provides an output signal at the emitter terminal of transistor Q8. This signal is provided on a line 60 and via a resistor R19 to the inverting terminal of an operational amplifier U1. The non-inverting terminal of amplifier U1 has its input determined through resistors R23, R24 and R25 which are connected between power and ground.

The signal generated at the output of amplifier U1 is passed on a line 62 through a resistor R21 and a resistor R26 to the base terminal of a transistor Q10. Transistor Q10 operates in a transconductance mode that provides an output current in accordance with the input voltage signal received from the amplifier U1. The output current developed at the collector terminal of the transconductance transistor Q10 is applied on a line 64 to the center leg of the current oscillator circuit 54. In this way, the gain in the circuit is dynamically adjusted to maintain oscillation of the sensor element and of the circuit.

The output signal on the line 62 which is proportional to the gain change for the circuit is also supplied through a resistor R21 to a Vdamping output terminal at a line 66. This signal corresponds to the detected viscosity density product.

In accordance with the invention, the sensing circuit 50 provides additional signals as well. For example, As seen in FIG. 5, a temperature sensor integrated circuit U2 provides an output signal on a line 68. In the preferred implementation, the temperature sensor IC is a type LM35 manufactured by National Semiconductor. The temperature output terminal 68 is also coupled through a resistor R33 and a capacitor C18 to ground. The signal on line 68 is available for use by the system.

In addition, a probe sense circuit 70 including a resistor matrix of resistors R31 and R32 coupled between +5 volts and ground provides a probe sense signal on a line 72. This signal is obtained in order to recognize variations in voltage provided by the power supply and also to recognize the sensing probe utilized.

The sensing circuit 50 also provides a frequency sensing signal indicative of the frequency of oscillation of the sensing element at an output terminal 74. In particular, the signal generated at the line 56 is provided through a resistor R2 to the base of a transistor Q5.The collector terminal of transistor Q5 is connected to +5 volts. The emitter terminal is connected through a resistor R1 to ground. The emitter terminal is also coupled through a filter capacitor C1 to the output line 74. This signal to provide analysis based on the frequency of oscillation.

The various component values for the sensing circuit are shown in Table I following:

TABLE I

| Element | Type, Value or Rating |
| --- | --- |
| Q1, Q2, Q3, Q4, Q5, Q6, Q8, Q9, Q10 | MMBR5179 |
| Q7 | MRF5211 |
| U1 | LT10130 |
| U2 | LM35 |
| D1, D2 | LT1009S8 |
| R1 | 110 |
| R2 | 3.09K |
| R3, R11, R25 | 2.05K |
| R4 | 196K |
| R5 | 205 |
| R6 | 9.09K |
| R7 | 619 |
| R8 | 590 |
| R9, R10 | 11.5K |
| R12 | 154 |
| R14 | 348 |
| R15 | 3.48K |
| R16, R18 | 11K |
| R17 | 30.1K |
| R19, R20 | 20K |
| R21 | 649 |
| R22 | 750 |
| R23 | 10.5K |
| R24 | 3.32K |
| R26 | 549 |
| R27 | 51.1 |
| R32 | 100K |
| R33 | 75 |
| L1 | 1 $\mu$H |
| L3 | 22 $\mu$H |
| C1, C3, C9, C10, C12, C15, C16, C17 | .1 $\mu$F |
| C2, C6, C7, C8, C13, C14 | .01 $\mu$F |
| C4 | .001 $\mu$F |
| L5A-B | 470 pF |
| C11, C18 | 1 $\mu$F |

According to one specific feature of the invention, component values of the sensing circuit are chosen in order to match sensor geometries and are adapted to measure various viscosity ranges. Due to the interface of the sensor probe 22 with the electrical control circuit, it is contemplated that various sensor probes may be interchanged as desired depending on the particular fluid under analysis. In this regard, the values of resistors R13, R28, R29 and R31 and inductor L2 may be varied. The values of resistor R30 and capacitor C5C are chosen as a function of the sensor geometry.

Figure 6:
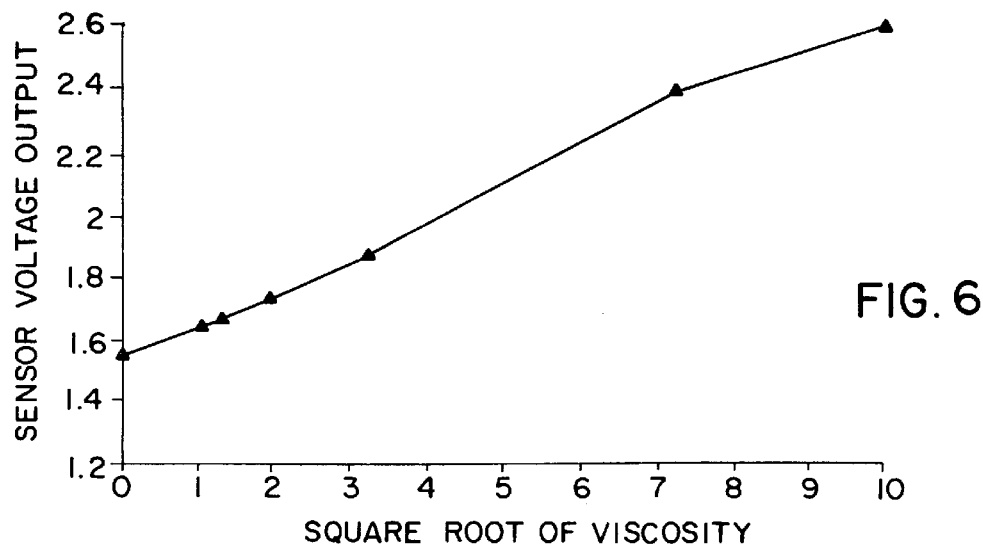
FIG. 6 is an output sensing voltage shown as a function of the square-root of viscosity of a fluid.

FIG. 6 illustrates the output voltage provided at the line 66 as a function of square root of viscosity of the fluid being analyzed. As shown there, the sensor construction according to the preferred embodiment of the invention provides a relatively linear voltage variation over the range of viscosities of the fluid under analysis.

In accordance with another particular feature of the invention, the characteristics of the sensor are calibrated in order to relate the sensed output voltage to the viscosity density product.

Figure 7:
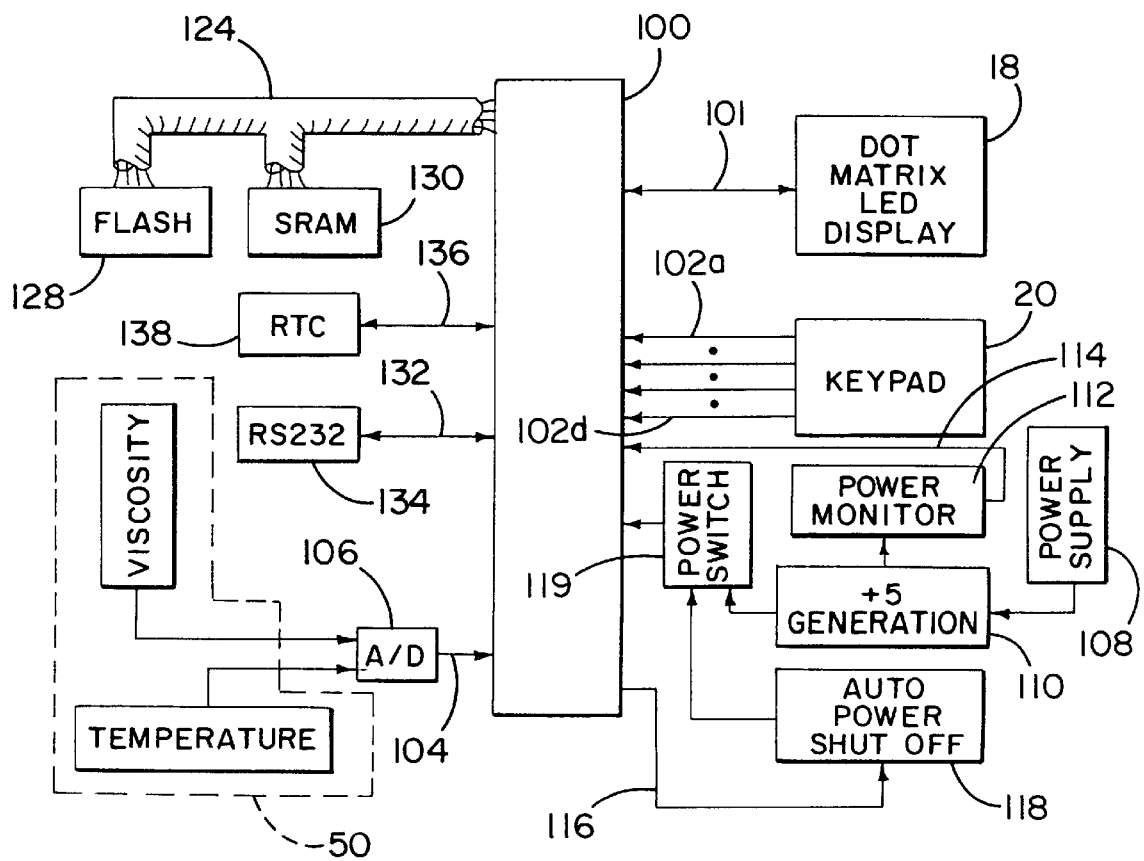
FIG. 7 is a simplified block diagram of an electrical control system suitable for utilizing the sensing signals provided from the sensing circuit of FIG. 5.

FIG. 7 is a system block diagram that may be utilized in conjunction with the sensor construction of the invention. This embodiment utilizes a microprocessor or CPU 100 in conjunction with appropriate circuitry to obtain sensing data from the sensing circuit 50. This data may be manipulated and then provided as output in various formats to the display 18 via a line 101. In the preferred embodiment, a Seiko LCD graphics display with controller circuit is utilized. Alternatively, the data may be stored or transported to other processing equipment such as a personal computer.

As shown in FIG. 7, the CPU 100 receives input information on the lines 102*a–d* from the keypad 20 and its related interface circuitry. In the preferred implementation, the CPU 100 is a Motorola micro-controller. The keypad is preferably interfaced to the CPU 100 through a 16-keypad encoder circuit with associated logic circuitry to ensure that the key depressed will be latched until it is read by the CPU as will be understood by those skilled in the art.

The CPU is also connected via a line 104 to an analog-to-digital A/D converter IC 106. The A/D converter 106 is a TLC2534 A/D that provides 12-bit resolution with 11 analog channels. The A/D converter 106 receives the viscosity-density sensing signal from the sensing circuit 50 on the line 66. As noted above, this signal is indicative of the sensed viscosity. The A/D converter provides a digital data stream to the CPU 100. The A/D converter 106 also receives the output signal on the line 68 provided by the temperature sensor and provides digital data in a serial fashion to the CPU 100 on the line 104.

In accordance with another particular feature of the invention, the unit is powered by either an external conventional AC line source or an internal battery such as a 7.2 volts NiHM battery pack, denoted by a block 108. Due to the components chosen, the unit dissipates very low power. The power supplied by either source is regulated to +5.0 volts by a regulator circuit 110. A low voltage inhibit or power monitoring circuit 112 detects when the voltage drops below 4.6 volts. Preferably, a warning light is triggered to indicate the need for battery recharge. In addition, this circuit provides a system reset signal to the CPU 100 on a line 114 in order to prevent the CPU 100 from entering an indeterminate state. In addition, the CPU 100 provides a command signal on a line 116 to a power shutoff switching circuit 118 when no key has been selected for a selected time interval. The regulator circuit 110 and power shutoff switching circuit 118 apply signals to a power switch 119 to effect shutoff of the system. The CPU 100 optionally receives information from the probe sense circuit 70 located on the sensor probe and notify the user as desired. In these instances, instrument power may also be turned off.

The CPU 100 is also connected via an address/data bus denoted by the lines 124 with FLASH memory 128 and to RAM memory 130. The FLASH memory 128 preferably contains the program that is executable by the CPU 104. One advantage of utilizing FLASH memory is that the instrument may be specially programmed without exchange of circuitry. In this regard, the CPU 100 is also connected by a line 132 to a circuit 134 that is adapted to transmit and receive data in an RS 232 data format. Thus, as an example, other programming features or functions may be downloaded into the FLASH memory 128 for greater flexibility.

Likewise, the CPU 100 is preferably connected via a line 136 to a real time clock integrated circuit (RTC) 138. The RTC 138 includes a real time clock as well as watchdog and interval timer so that such information may be obtained by the unit. The RTC 138 also includes memory that may be utilized to store sensing data and/or calibration data as desired.

In operation, the CPU 100 operates under the control of the program contained in the FLASH memory 128 to receive digital input signals from the keypad and associated circuitry 20 via the lines 102*a–d*. These signals are based on user input and selection. The CPU 100 also receives raw digital sensing data supplied by the A/D converter 106 including data relating to the absolute viscosity of the fluid under analysis as well as the temperature of the fluid. Optionally, the CPU 100 receives data corresponding to the frequency of oscillation of the sensing element 30.

The CPU 100 performs logical operations with data supplied by the A/D converter 106 in conjunction with the RAM 130 and provides appropriate output signals on the line 101 to the display 18. For example, the CPU 100 calculates the kinematic viscosity (ν) in centiStokes (cSt) from the viscosity sensing data. Inasmuch as the absolute viscosity (η) is determined by the relationship $v=\eta/\rho$, where ρ is the density of the fluid, the CPU 100 also calculates the absolute viscosity (η) in centipoise (cP) when the density (ρ) is expressed in grams per cubic centimeter (mass to density ratio) via an appropriate internal conversion algorithm. For calculating this information, the CPU 100 also utilizes calibration data contained in the NV RAM of the RTC circuit 138. The sensing data may also be stored in the NV RAM of the RTC circuit 138 and accessed by the CPU 100 or downloaded to other processing equipment as desired.

Figure 8:
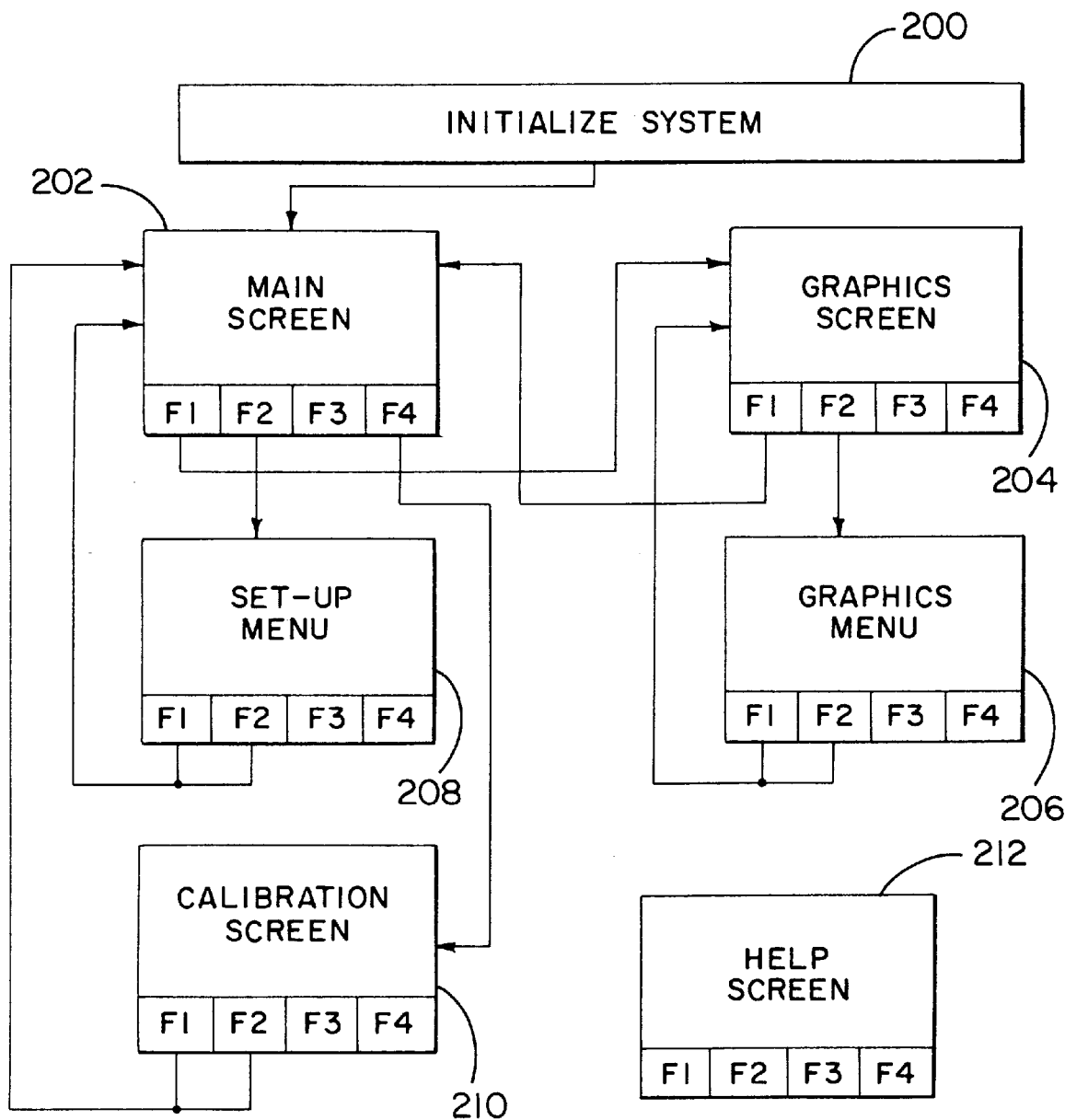
FIG. 8 is a user interface flow diagram that may be used to implement the various functions performed by the system of FIG. 7.

FIG. 8 illustrates a user interface flow diagram of the various functions performed by the instrument. The system begins by initializing the various components of the system at a block 200. Next, the system branches to a Main Screen block 202 and displays a Main menu wherein various optional modes can be accessed. For example, when a function key F1 is selected, the system branches to a block 204 wherein a Graphics Screen mode of operation is performed. In this mode, a graphics menu may be selected by selection of an appropriate function key F2. The system then branches to a Graphics Menu screen mode at a block 206. Alternatively, the Main Screen display may be selected at the Graphics Screen denoted by the block 204.

On the other hand, if at the Main Screen denoted by the block 202, a Setup Menu display mode is selected by an appropriate function key F2, the system branches to a Setup Menu screen denoted by a block 208.

Similarly, when the appropriate function key F4 is selected from the Main Menu denoted by the block 202, the system branches to a Calibration Screen denoted by a block 210 in order to present a Calibration Screen mode of operation. In this mode, the system displays to the user various calibration functions. A user may analyze a known sample together with data provided with the sample in order to input new calibration data to the system. Selection of appropriate function keys F1 or F2 returns the system to the Main Screen block 202.

In the preferred embodiment, the user may select a Help Screen denoted by a block 212 by selection of an appropriate function key F3.

Figure 9A:
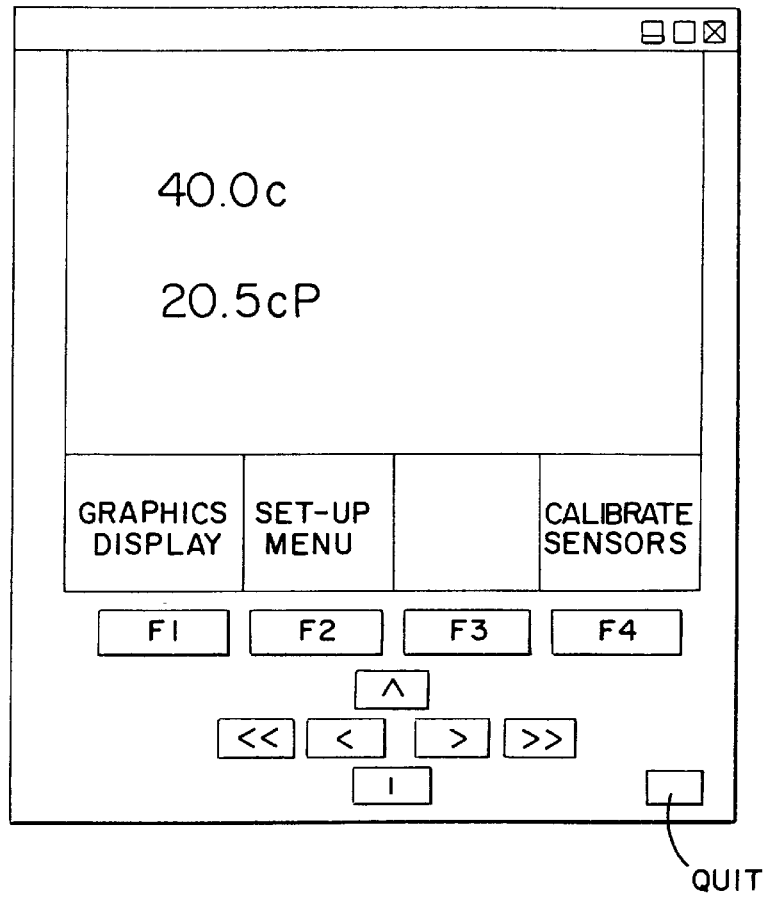
FIGS. 9A–C are display formats that may used according to a preferred embodiment of the invention.
Figure 9B:
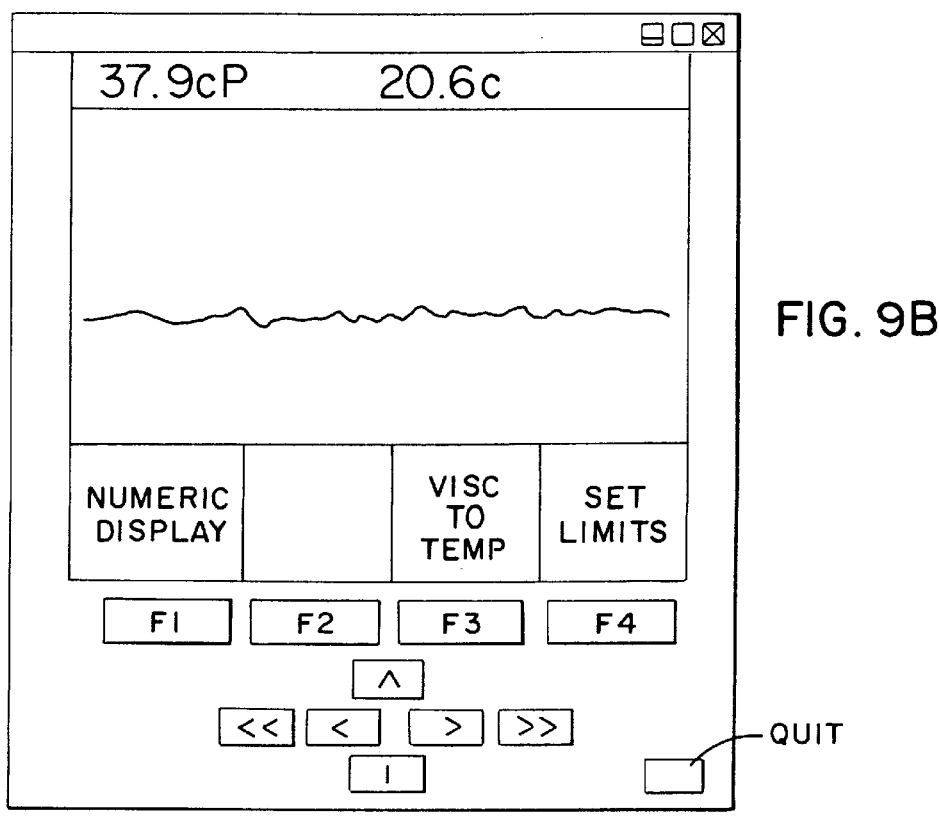
Figure 9C:
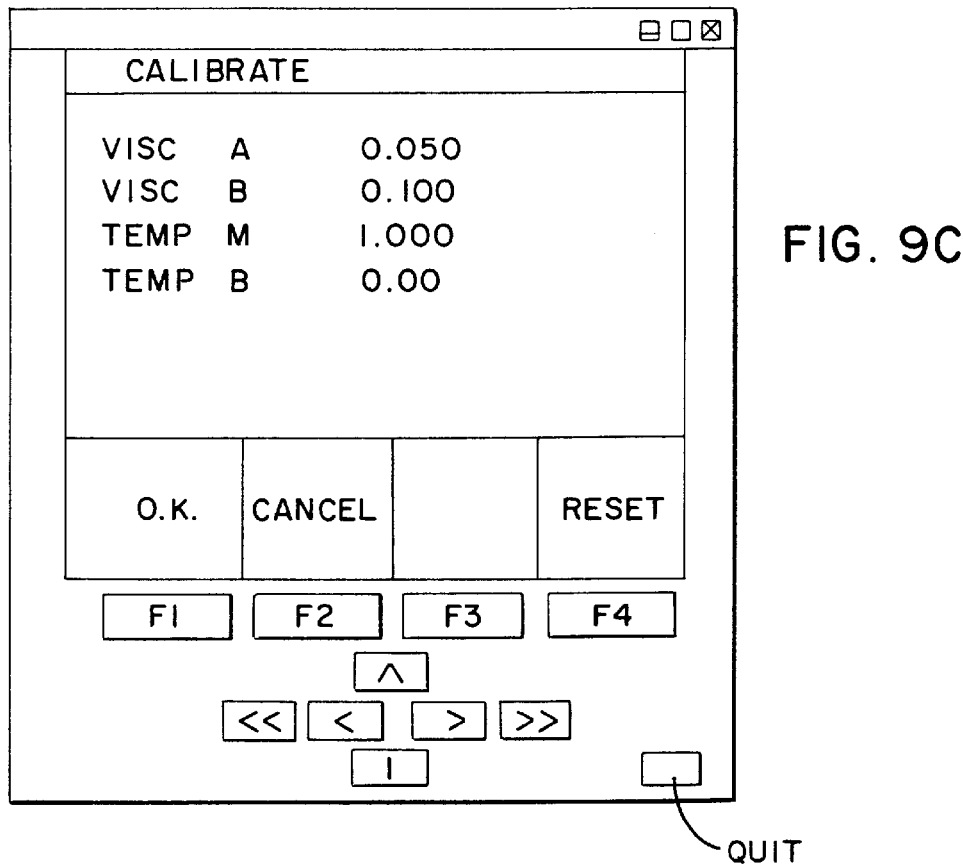
Figure 10A:
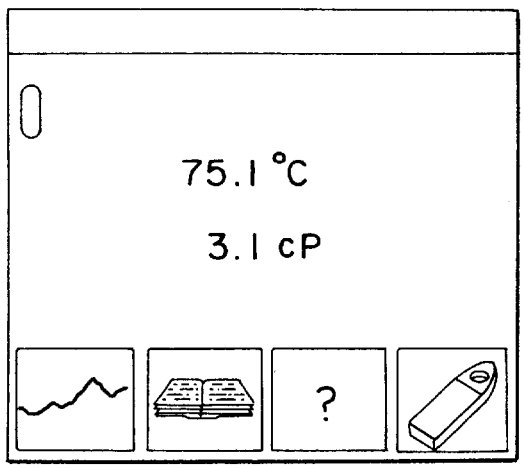
FIGS. 10A–D are alternative display formats that may be utilized according to the present invention.
Figure 10B:
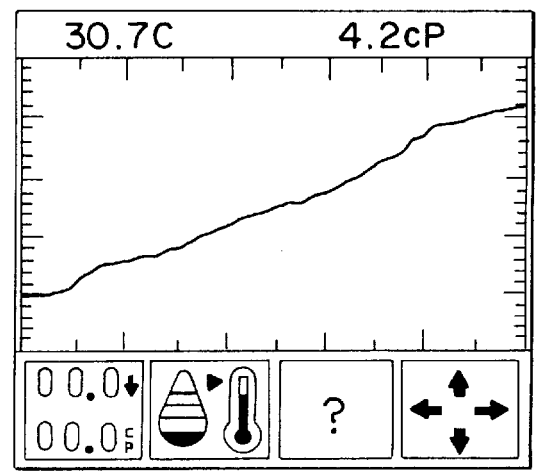
Figures 10C, 10D:
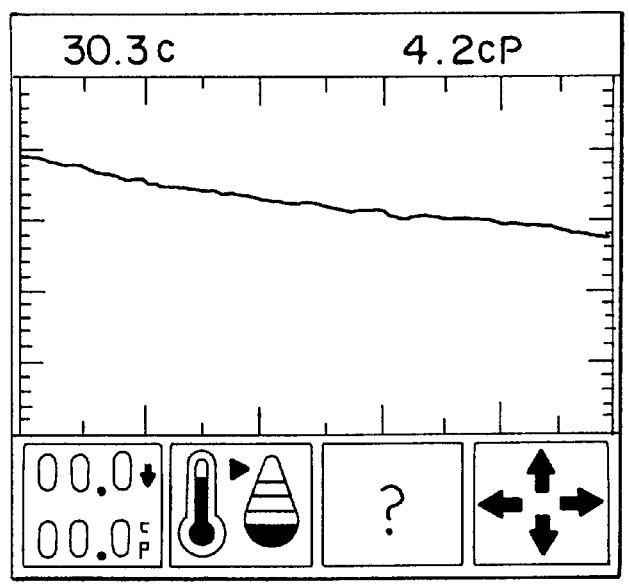

FIGS. 9A–C show various displays corresponding to the modes of operation described above in conjunction with FIG. 8. As shown in FIG. 9A, the unit may display numeric values of viscosity and temperature. Alternatively, the unit may be placed in the graphics mode such that a graphical representation of viscosity is displayed as is shown in FIG. 9B. FIG. 9C illustrates the system in a calibration mode.

Alternatively, the invention contemplates other graphical interfaces to be utilized. Exemplary screen displays using an icon-based selection are shown in FIGS. 10A–D. The screen displays for the icon-based alternative embodiment correspond to the various modes of operation described above. With this embodiment, input may be provided with a touch-screen display or with icon-labeled function keys.

Figure 13:
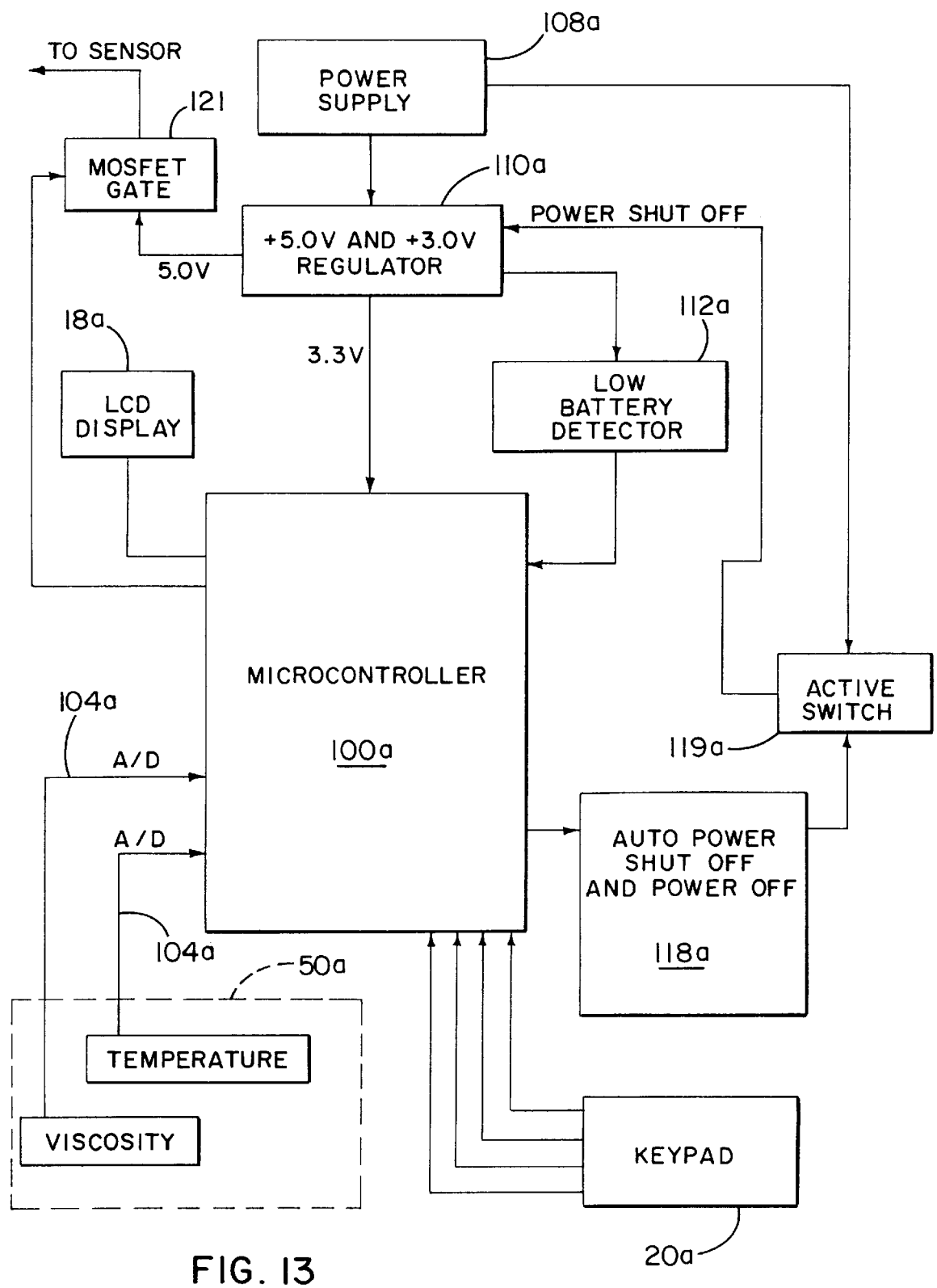
FIG. 13 is an overall block diagram representation of the embodiment shown in FIGS. 11 and 12.

Referring now to FIGS. 11–13, there is shown an alternative embodiment of a unitary viscometer construction 10a in accordance with the invention. Items similar to those described above in conjunction with the embodiment of FIGS. 1–10 have been given similar reference numerals with the distinguishing suffix "a" added. The viscometer 10a has a lightweight instrument housing 24a which is formed by joining a pair of matingly engageable elongated housing pieces 40a, 42a (see FIG. 12). In this embodiment, the viscometer 10a may be viewed as a "pocket viscometer" in that its overall dimension is on the order of nine inches by one and three fourths inches with a profile of about one inch or less.

In this alternative construction, a sensor probe 22a which is of the same construction described above is disposed within the instrument housing 24a. In addition, an electrical control circuit including a user input interface 20a having one or more pushbutton keys such as a "Mode" key for selecting various viscosity measurements (i.e., absolute or kinematic), "t(plus)" and "-" sequencing keys and a "Temp." selection key. The user interface 20a is located within the housing 24a. In this regard, an LCD instrument display 18a is disposed to provide viscosity in centiStokes, centiPoise and the viscosity density product within a selected range. The temperature of the liquid under investigation may also be displayed in degrees Celsius or Fahrenheit. The display 18a is located on a facing surface of the instrument housing 24a.

As with the embodiment described above, the sensor probe 22a is a crystal resonator type sensor. When in use, the sensor probe 22a is in contact with the fluid under investigation. The sensor 22a has an exposed sensing element portion 30a so that it may be placed in contacting relation with, through immersion into, the fluid of interest. In the preferred embodiment, the accuracy is at least within five percent of full scale. Similarly, a temperature sensor (not shown) is disposed in the housing 24a. The details of the sensor probe 22a and the various components of the circuitry used in connection therewith are preferably the same as described above in connection with FIGS. 3–5, by way of example. Thus, the signals developed by the sensing element 30a and temperature sensor correspond to the detected viscosity density product, the frequency of oscillation of the sensor element, and the temperature of the fluid as described above.

FIG. 13 illustrates a block diagram for the system control of the one-piece portable sensor construction. As shown, this embodiment utilizes a micro-controller 100a which is disposed to receive viscosity and temperature sensing data from a viscosity sensing circuit 50a, which is also preferably the same as the sensing circuit 50 described above. This data is ultimately provided as output to the instrument display 18a. Similarly, the micro-controller 100a receives input information from the user interface keypad 20a.

In accordance with one feature of the invention, the instrument 10a includes power detection circuitry. In this regard, a battery power supply provides an output voltage to a regulator circuit 110a which, in turn, provides regulated constant voltages to the system (i.e., five volts for the sensing circuit 50a and 3.3 volts for the control circuit). A power monitoring circuit 112a detects the voltage levels provided by the regulator circuit 110a. When the voltage levels drop beneath a threshold, the detection circuitry 112a provides an appropriate signal to the micro-controller 100a. In response, the micro-controller 100a provides output signals to an auto-power shutoff circuit 118a to thereby actuate an active switch 119a. When appropriate, the switching circuit provides a power shutoff signal to the regulator circuit 110a.

The regulator circuit 110a also provides an appropriate signal, i.e., five (5) volts, via a MOSFET switching transistor 119 to the sensor circuitry 50a. Similarly, the micro-controller 110a provides an appropriate signal to the gate input of the MOSFET switching transistor 121. When the system power is on and no abnormal conditions are present, the MOSFET switching transistor 121 conducts so that the sensing circuitry is operable. On the other hand, when an abnormal condition such as low power is detected, the micro-controller 100a provides a signal to the MOSFET switching transistor 121 to thereby disable the sensing circuitry 50a.

In operation, the viscometer 10a is programmed to automatically display the sensed viscosity when the unit is turned on via depression of the appropriate pushbutton input key. Depressing the mode key scrolls the user between various viscosity units, the viscosity density product, a calibration which operates as described above, and a recall of collected data. The system is programmed to scroll within the different modes and change the calibration constant and/or the density constant by receipt of input from the "t" and "-" input keys. The system stores the calibration constant in memory located with the micro-controller 100a to avoid recalibration when the unit is off.

Various advantages flow readily from the invention. That is, where prior art measuring instruments have required relatively large fluid samples in order to provide a viscosity measurement, the invention can perform the same measurement with 10 ml of fluid or less. The invention may also be packaged in an entirely portable construction that weighs less than 2 lbs. in one embodiment, and less than 1.5 lbs. in a second embodiment. Similarly, slight power is consumed by the invention. Thus, the invention is readily transportable and adapted for use in many situations.

Accordingly, a viscosity measurement device meeting the aforestated objectives has been described. The device is readily portable and provides an easy-to-use instrument which is relatively simple in construction and design, while being quite versatile in operation. Of course, those skilled in the art will understand that other modifications may be incorporated, particularly upon consideration of the foregoing teachings. For example, the instrument may be interconnected with a personal computer or other processing device which can further manipulate the acquired data with the inclusion of appropriate interface circuitry and software. Accordingly, the invention is not intended to be limited to the specific embodiments described herein. To the contrary, it is intended that modifications to the invention and equivalents are also intended to be covered as set forth by the appended claims, which are made part of this disclosure.

What is claimed is:

1. A portable one-piece viscosity measuring device comprising:

an instrument body;

a sensor disposed within the instrument body, including a thickness shear mode resonator having a portion in contacting relation with the fluid to be analyzed, a sensor circuit operably connected with the resonator disposed to generate first sensing signals corresponding to the damping of the resonator due to the fluid to be analyzed, and a temperature sensor disposed disposed to generate second sensing signals indicative of the temperature of the fluid; and a microcontroller-based control circuit located in the instrument body disposed to receive the first and second sensing signals, to generate a viscosity value from the first and second sensing signals, to generate a viscosity value from the first and second sensing signals, and to provide an output to a display.

2. The invention as in claim 1 further comprising a power supply disposed in the instrument body.

3. The invention as in claim 1 wherein said control circuit includes means for storing calibration data indicative of the sensor.

4. The invention as in claim 1 wherein said resonator comprises a micromachined disk fabricated from quartz and a pair of electrodes located on opposed sides of the disk, the sensor circuit coupled with the electrodes and disposed to operate at a resonant frequency of oscillation.

5. The invention as in claim 4 wherein the sensor circuit is an oscillator circuit disposed to operate at the resonant frequency of oscillation of the sensing element, to measure the damping of the frequency of oscillation based on fluid viscosity and to provide a sensing voltage corresponding thereto.

6. The invention as in claim 5 wherein said control circuit further includes means disposed to obtain the second sensing signals from the sensing circuit and to calculate viscosity based on the first and second sensing signals.

7. The invention as in claim 6 wherein said sensor circuit includes means for sensing a current required to maintain the sensing circuit at the frequency of oscillation of the sensing element.

8. A portable one-piece viscosity measuring device comprising:

an instrument body;

a viscosity sensor disposed within the instrument body, including a resonator having a portion immersed in the fluid to be analyzed, a sensor circuit operably connected with the resonator disposed to generate first sensing signals corresponding to the damping of the frequency of oscillation of the resonator when immersed in the fluid to be analyzed;

a temperature sensor disposed to generate second sensing signals indicative of the temperature of the fluid; and a control circuit located in the instrument body disposed to generate a viscosity value from the first and second sensing signals and to provide an output to a display.

* * * * *

UNITED STATES PATENT AND TRADEMARK OFFICE
CERTIFICATE OF CORRECTION

PATENT NO.    : 6,141,625
DATED         : October 31, 2000
INVENTOR(S)   : Smith et al.

Page 1 of 1

It is certified that error appears in the above-identified patent and that said Letters Patent is hereby corrected as shown below:

Column 2,
Line 20, delete "electromechanical" and insert -- electro-mechanical --.
Line 46, delete "samples" and insert -- sample --.

Column 3,
Line 9, insert -- of -- between "embodiment" and "the".

Column 6,
Line 5, delete "As" and insert -- as --.

Column 8,
Line 1, delete "notify" and insert -- notifies --.
Line 39, delete "centipoise" and insert -- centiPoise --.

Column 6,
Line 26, delete "to provide" and insert -- is used to the --.
Line 27, insert -- of the sensing element 30 -- after "oscillation".

Column 11,
Line 18, delete "disposed" second occurance.

Signed and Sealed this

Thirteenth Day of November, 2001

Attest:

*Nicholas P. Godici*

NICHOLAS P. GODICI
*Attesting Officer*   *Acting Director of the United States Patent and Trademark Office*